US012737879B2

(12) United States Patent
Liu et al.

(10) Patent No.: US 12,737,879 B2
(45) Date of Patent: Sep. 15, 2026

(54) MACHINE LEARNING FOR DETECTION OF DISEASES FROM EXTERNAL ANTERIOR EYE IMAGES

(71) Applicant: Google LLC, Mountain View, CA (US)

(72) Inventors: Yun Liu, Mountain View, CA (US); Naama Hammel, Sunnyvale, CA (US); Akinori Mitani, Mountain View, CA (US); Derek Janme Wu, Mountain View, CA (US); Ashish Dilipchand Bora, Sunnyvale, CA (US); Avinash Vaidyanathan Varadarajan, Los Altos, CA (US); Boris Alekandrovich Babenko, Sunnyvale, CA (US)

(73) Assignee: GOOGLE LLC, Mountain View, CA (US)

( * ) Notice: Subject to any disclaimer, the term of this patent is extended or adjusted under 35 U.S.C. 154(b) by 592 days.

(21) Appl. No.: 18/011,597

(22) PCT Filed: Nov. 2, 2021

(86) PCT No.: PCT/US2021/057659
§ 371 (c)(1),
(2) Date: Dec. 20, 2022

(87) PCT Pub. No.: WO2022/094446
PCT Pub. Date: May 5, 2022

(65) Prior Publication Data

US 2023/0230232 A1 Jul. 20, 2023

Related U.S. Application Data

(60) Provisional application No. 63/187,562, filed on May 12, 2021, provisional application No. 63/108,712, filed on Nov. 2, 2020.

(51) Int. Cl.
*G06K 9/00* (2022.01)
*A61B 3/12* (2006.01)
(Continued)

(52) U.S. Cl.
CPC .......... *G06T 7/0012* (2013.01); *A61B 3/1241* (2013.01); *G16H 30/40* (2018.01);
(Continued)

(58) Field of Classification Search
None
See application file for complete search history.

(56) References Cited

U.S. PATENT DOCUMENTS 10,468,142 B1 11/2019 Shousha et al.
2019/0110753 A1 4/2019 Zhang et al.
(Continued)

FOREIGN PATENT DOCUMENTS

CN 111820863 10/2020
WO WO-2019240567 A1 * 12/2019 .......... A61B 3/0025
(Continued)

OTHER PUBLICATIONS

International Preliminary Report on Patentability for Application No. PCT/US2021/057659, mailed May 11, 2023, 7 pages.
(Continued)

*Primary Examiner* — Wei Wen Yang
(74) *Attorney, Agent, or Firm* — DORITY & MANNING, P.A.

(57) ABSTRACT

The present disclosure is directed to systems and methods that leverage machine learning for detection of eye or non-eye (e.g., systemic) diseases from external anterior eye images. In particular, a computing system can include and use one or more machine-learned disease detection models to provide disease predictions for a patient based on external anterior eye images of the patient. Specifically, in some
(Continued)

example implementations, a computing system can obtain one or more external images that depict an anterior portion of an eye of a patient. The computing system can process the one or more external images with the one or more machine-learned disease detection models to generate a disease prediction for the patient relative to one or more diseases, including, as examples, diseases which present manifestations in a posterior of the eye (e.g., diabetic retinopathy) or systemic diseases (e.g., poorly controlled diabetes).

29 Claims, 11 Drawing Sheets

(51) Int. Cl.

| | |
|---|---|
| ***G06T 7/00*** | (2017.01) |
| ***G16H 30/40*** | (2018.01) |
| ***G16H 50/50*** | (2018.01) |

(52) U.S. Cl.
CPC ... *G16H 50/50* (2018.01); *G06T 2207/20081* (2013.01); *G06T 2207/20084* (2013.01); *G06T 2207/30041* (2013.01)

(56) References Cited

U.S. PATENT DOCUMENTS

| | | | | |
|---|---|---|---|---|
| 2020/0069175 | A1 | 3/2020 | Kumagai et al. | |
| 2020/0349710 | A1 | 11/2020 | Paschalakis et al. | |
| 2021/0244272 | A1* | 8/2021 | Lim | G06N 3/047 |
| 2024/0341589 | A1 | 10/2024 | Hemert | |

FOREIGN PATENT DOCUMENTS

| | | | | |
|---|---|---|---|---|
| WO | WO-2020160097 A1 * | 8/2020 | | A61B 3/0033 |
| WO | WO 2020/200087 | 10/2020 | | |

OTHER PUBLICATIONS

Babenko et al., "Detecting Hidden Signs of Diabetes in External Eye Photographs", arXiv:2011.11732, 43 pages.

Babenko et al., "Detection of Signs of Disease in External Photographs of the Eyes via Deep Learning", Nature BioMedical Engineering, vol. 6, Dec. 2022, 24 pages.

Extended European Search Report for Application No. EP 21887759.5, mailed Sep. 26, 2024 19 pages.

Karakaya et al., "Comparison of Smartphone-based Retinal Imaging Systems for Diabetic Retinopathy Detection Using Deep Learning", 16th Annual Conference of the Midsouth Computational Biology & Bioinformatics Society, Mar. 28-30, 2019, Birmingham, AL, USA, 18 pages.

Pour et al., "Automatic Detection and Monitoring of Diabetic Retinopathy Using Efficient Convolutional Neural Networks and Contrast Limited Adaptive Histogram Equalization", IEEE Access, vol. 8, 2020, 6 pages.

Teo et al., "Eyeing Severe Diabetes Upfront", Nature BioMedical Engineering, vol. 6, Dec. 2022, 2 pages.

International Search Report for Application No. PCT/ US2021/ 57659, mailed on Jan. 31, 2022, 2 pages.

Chinese Search Report Corresponding to Application No. 2021800747107 on Jul. 8, 2025.

* cited by examiner

204
External Image(s) of Anterior Eye
202
Disease Detection Model
206
Disease Prediction(s)

300
302
Disease Detection Model
304
306
204
External Image(s) of Anterior Eye
Image Embedding Portion
Disease Prediction Portion
206
Disease Prediction(s)

MACHINE LEARNING FOR DETECTION OF DISEASES FROM EXTERNAL ANTERIOR EYE IMAGES

CROSS-REFERENCE TO RELATED APPLICATIONS

This application is based upon and claims the right of priority under 35 U.S.C. § 371 to International Application No. PCT/US2021/057659 filed on Nov. 2, 2021, which claims priority to and the benefit of each of U.S. Provisional Patent Application No. 63/108,712, filed Nov. 2, 2020 and U.S. Provisional Patent Application No. 63/187,562, filed May 12, 2021. Applicant claims priority to and the benefit of each of such applications and incorporates all such applications herein by reference in its entirety.

FIELD

The present disclosure relates generally to machine learning. More particularly, the present disclosure relates to machine learning for detection of eye or non-eye (e.g., systemic) diseases from external anterior eye images.

BACKGROUND

Disease detection and diagnosis often requires specialized equipment and trained medical professionals to interpret the findings. However, this specialized equipment is often expensive, unwieldy, requires highly trained operators, and/or not widely available.

As one example, diabetic retinopathy (DR) screening programs typically require a professional to use a ophthalmoscope or fundus camera to examine (e.g., capture and analyze images of) the posterior (i.e., back) part of the eye (e.g., the retinal fundus). For example, the 2019 American Academy of Ophthalmology Diabetic Retinopathy Preferred Practice Pattern (https://www.aaojournal.org/article/S0161-6420(19)32092-5/pdf) advises that an initial examination for diabetic retinopathy should include both Slit-lamp biomicroscopy and thorough fundoscopy, including stereoscopic examination of the posterior pole. Further, the Preferred Practice Pattern indicates that a dilated pupil is preferred to ensure optimal examination of the retina. This extensive examination of the posterior of the eye is typically required for various different disease manifestations present in the posterior of the eye, including, for example, diabetes-related blood vessel compromise, such as microaneurysms.

Recently, machine-learning techniques have been used to automatically detect certain disease manifestations present in the posterior of the eye when given retinal fundus photographs as input. Thus, when fundus imagery for a patient is available, certain recently proposed computerized techniques may enable efficient triaging or early screening for disease manifestations in the patient's eye.

However, these machine-learning techniques still require the use of fundus imagery or other complex imagery that depicts the posterior of the eye. The use of a fundus camera to obtain such fundus imagery requires high skills from the photographer, is costly and time-consuming, and is therefore not ideal for primary screening by non-experts.

One example of such a machine learning-based approach is provided in Li et al., Deep learning for detecting retinal detachment and discerning macular status using ultra-widefield fundus images. *Commun Biol* 3, 15 (2020). https://doi.org/10.1038/s42003-019-0730-x. Specifically, Li et al. describe a cascaded deep learning system based on the ultra-widefield fundus images for automated retinal detachment detection and macula-on/off retinal detachment discerning. However, Li et al., indicate that "[t]o efficiently screen RD [retinal detachment] using AI [artificial intelligence], the prerequisite is to obtain fundus images covering the peripheral retina."

Thus, both current expert medical procedure and cutting edge experimental approaches have expressed a strong belief that fundus imagery is required (i.e., a "prerequisite") to successful detection of disease manifestations in the posterior of the eye.

As such, although certain recent machine learning-based diagnostic techniques expand the diagnostic information that can be obtained from fundus photographs, they still require fundus imagery as a prerequisite. Therefore, the burden of costly specialized fundus cameras, skilled imaging technicians, and oftentimes mydriatic eye drops to dilate (enlarge) the patient's pupils limits the use of these diagnostic techniques to eye clinics or primary care facilities with specialized equipment.

SUMMARY

Aspects and advantages of embodiments of the present disclosure will be set forth in part in the following description, or can be learned from the description, or can be learned through practice of the embodiments.

One example aspect of the present disclosure is directed to a computing system for detection of diseases from external anterior eye images. The computing system includes one or more processors and one or more non-transitory computer-readable media that collectively store: one or more machine-learned disease detection models configured to provide disease predictions based on external anterior eye images; and instructions that, when executed by the one or more processors, cause the computing system to perform operations. The operations include obtaining one or more external images that depict an anterior portion of an eye of a patient. The operations include processing the one or more external images with the one or more machine-learned disease detection models to generate a disease prediction for the patient relative to one or more diseases. The operations include providing the disease prediction for the patient relative to the one or more diseases as an output.

Another example aspect of the present disclosure is directed to a computer-implemented method for training a machine-learned disease detection model to provide disease predictions based on external anterior eye images. The method includes obtaining one or more external images that depict an anterior portion of an eye of a patient, wherein one or more ground truth disease labels are associated with the one or more external images. The method includes processing the one or more external images with one or more machine-learned disease detection models to generate a disease prediction for the patient relative to one or more diseases. The method includes evaluating a loss function that compares the disease prediction for the patient with the one or more ground truth disease labels. The method includes modifying one or more values of one or more parameters of the machine-learned disease detection models based at least in part on the loss function.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which.

Figure 1:
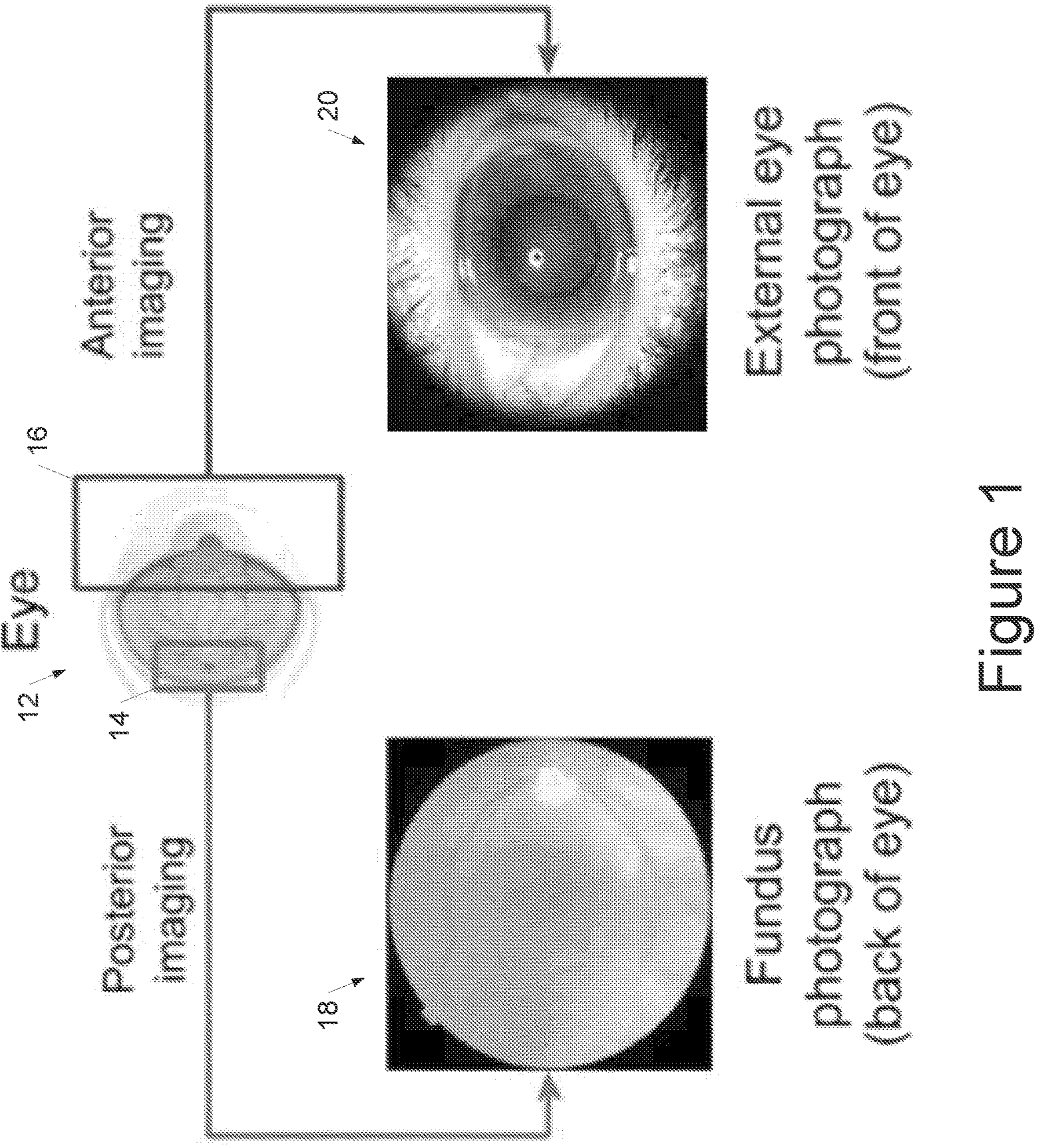
FIG. 1 provides a graphical depiction of an eye of a patient according to example embodiments of the present disclosure.

Reference numerals that are repeated across plural figures are intended to identify the same features in various implementations.

DETAILED DESCRIPTION

Overview

Generally, the present disclosure is directed to systems and methods that leverage machine learning for detection of eye or non-eye (e.g., systemic) diseases from external anterior eye images. In particular, a computing system can include and use one or more machine-learned disease detection models to provide disease predictions for a patient based on external anterior eye images of the patient. Specifically, in some example implementations, a computing system can obtain one or more external images that depict an anterior portion of an eye of a patient. The computing system can process the one or more external images with the one or more machine-learned disease detection models to generate a disease prediction for the patient relative to one or more diseases, including, as examples, diseases which present manifestations in a posterior of the eye (e.g., diabetic retinopathy). The computing system can provide the disease prediction for the patient as an output (e.g., to the patient, to a medical professional, to an electronic medical record system, and/or various other systems or processes). Thus, in contrast to current medical and experimental diagnostic approaches which require the availability of posterior eye images to detect posterior eye disease manifestations, example implementations of the present disclosure are able to detect such diseases directly from anterior eye images alone, which was heretofore believed to be impossible by experts in both the medical and data science fields.

In particular, example experimental results contained in U.S. Provisional Patent Application Nos. 63/108,712 and 63/187,562 empirically demonstrate the ability to diagnose diseases which manifest in a posterior of the eye (e.g., diabetic retinal diseases) using only external photographs of the front of the eye. Specifically, these example results indicate that external eye photographs contain information useful for the management of diabetic patients and may help prioritize diabetic patients for in-person screening. By using machine learning to enable detection of posterior-eye-manifesting or systemic diseases from frontal eye imagery alone, the systems and methods of the present disclosure obviate the need for a fundus camera or other complex posterior eye imaging system for routine screening, triaging of patients, or other instances of disease detection.

More particularly, example aspects of the present disclosure are directed to one or more machine-learned disease detection models configured to provide disease predictions based on external anterior eye images. The one or more machine-learned disease detection models can be trained or configured to provide a disease prediction relative to one or more diseases based on the external eye images.

In some implementations of the present disclosure, the one or more machine-learned disease detection models can be trained or configured to provide a disease prediction relative to one or more systemic diseases. Systemic diseases can include diseases which typically affect one or more organ systems and/or present manifestations throughout multiple portions of the body. As examples, the one or more systemic diseases can be or include a blood sugar control disease. For example, the blood sugar control disease can be or include diabetes and poorly controlled diabetes. As other examples, the one or more systemic diseases can be or include cardiovascular risk or adverse cardiac outcomes, hypertension, anemia, chronic kidney disease, sleep apnea, hypercholesterolemia/atherosclerosis, thyroid disease, hyperparathyroidism, chronic renal failure, gout, hyperlipidemia (elevated blood lipids), and/or other systemic diseases.

In some implementations of the present disclosure, the one or more machine-learned disease detection models can be trained or configured to provide a disease prediction relative to one or more disease manifestations in the eye. For example, the one or more disease manifestations can be or include one or more disease manifestations in a posterior of the eye. As examples, the one or more disease manifestations in the posterior of the eye can be or include diabetic retinopathy, diabetic macular edema, a microaneurysm, glaucoma, age-related macular degeneration, detached retina, cancer of the eye, and/or various forms of retinal disease.

The disease prediction provided by the one or more machine-learned disease detection models can take a number of different formats or measures. As one example, the disease prediction for the patient relative to the one or more diseases can be or include one or more predicted probabilities that the patient is respectively experiencing the one or more diseases. For example, an example disease prediction might indicate that a patient is, with 78% probability, currently experiencing (i.e., diagnosed to have) diabetes.

As another example, the disease prediction for the patient can be or include a predicted evaluation value for the patient. For example, the predicted evaluation value for the patient can be a prediction of a value that would be returned if the patient were evaluated using one or more tests useful for evaluating an eye or non-eye disease. As one example, the disease prediction for the patient relative to the one or more diseases can include a predicted hemoglobin A1c level for the patient, which can, for example, be used to assess or predict a diabetes diagnosis for the patient.

As another example, the disease prediction for the patient relative to the one or more diseases can be or include one or more predicted severity levels respectively for the one or more diseases. For example, an example disease prediction might indicate that a patient is diagnosed with a disease with a particular severity level out of a number of potential severity levels for the disease (e.g., level 2 out of 5 possible levels).

As yet another example, the disease prediction for the patient relative to the one or more diseases can be or include a progression prediction that predicts a time to event for one or more diseases. For example, an example disease prediction might indicate that a patient that is not yet demonstrating disease manifestations may begin demonstrating disease manifestations in six months. Progression predictions (e.g., time to event predictions) can be provided for any number of clinically meaningful events. Thus, the terms "diagnosis" and "detection" of diseases can include prognosis (e.g., whether a disease or outcome will happen in the future).

According to another aspect of the present disclosure, the one or more machine-learned disease detection models can generate the disease prediction based on one or more external images of the anterior (i.e., front) of the patient's eye. These external images can be captured by various different types of devices, including commonly-available cameras (e.g., as opposed to specialized ophthalmoscopes and fundus cameras), thereby enabling more widespread and efficient access to healthcare.

As one example, the one or more external images can be or include one or more images captured by a user device. For example, the user device may be operated by the patient at a time of capture of the one or more images captured by the user device. As examples, the user device can be a camera of a laptop, a camera of a smartphone (e.g., a front facing camera positioned on a same side of the smartphone as a display that depicts a viewfinder for the camera or a rear facing camera on the opposite side), an external webcam affixed to another user device, or other standalone cameras (e.g., point-and-shoots, DSLR, etc.).

However, although the systems and methods described herein can be used with commonly-available consumer-grade cameras, they can also be used with more sophisticated cameras or imaging devices. As examples, the one or more external images can be or include one or more images captured by a slit lamp camera or a fundoscopic camera operated to capture external anterior eye imagery.

In some implementations, to facilitate successful capture of the external images, a computing system or device (e.g., a user device such as a smartphone) can provide graphical, tactile, and/or auditory user feedback that assists the patient in aligning the anterior portion of the eye with a camera. For example, an image acquisition system can detect an eye/pupil/etc. in real time and can provide the feedback to the user. In one example, the feedback can include periodic audio alerts, where a frequency of the audio alerts increases as the alignment between the eye and camera improves. Directional feedback can be provided as well (e.g., "move the camera upwards").

In some implementations, the image acquisition system can automatically capture an image so that the user does not need to operate the image capture control on the camera device. Alternatively or additionally, the image acquisition system can record a video stream as the user moves the phone in front of their face, and then identify one or more of the video frames which have the best or suitable alignment or appearance (e.g., as measured by some metric including, for example, blurriness, motion, number of pixels attributable to the eye, a machine-learned metric, etc.).

In some implementations, the images provided to the disease detection model(s) can be pre-processed. For example, the one or more external images can be or include cropped portions that have been cropped from one or more larger images. For example, in some implementations, an image that depicts a larger portion of the patient (e.g., the patient's full body or upper torso and head) can be cropped to extract the portion that corresponds to the anterior of the patient's eye. In some implementations, preprocessing the image can include applying a segmentation model to identify and extract only the portions of the image that correspond to the patient's iris and/or pupil. In some implementations, user feedback can be solicited to assist in performing the cropping of the portion of the image that corresponds to the eye.

The example experimental results included in the incorporated provisional applications indicate that the proposed systems can provide accurate diagnoses even on limited resolution imagery. As examples, in some instances, the one or more external images may be one or more images having a resolution of 200×200 pixels or less, a resolution of 100×100 pixels or less, or a resolution of 75×75 pixels or less. This indicates that even when the patient's eye is not prominent within an original photograph, a smaller crop that corresponds to the eye may still be processed to generate the disease prediction.

The one or more machine-learned disease detection models can be various forms of machine-learned models. As an example, in some implementations, the one or more machine-learned disease detection models can be or include one or more convolutional neural networks. Example convolutional neural networks include ResNets and Inception networks.

In some implementations, an ensemble of skin condition classification models can be used according to an ensemble approach. For example, each respective skin condition classification model in the ensemble can make a respective prediction. A final prediction of the ensemble can be an aggregate (e.g., average) of the predictions from the multiple different models of the ensemble. In some implementations, each model in the ensemble is trained in the same manner.

In some implementations, the one or more machine-learned disease detection models can be or include one or more multi-headed neural networks that each have a plurality of heads that respectively output a plurality of predictions. As one example, at least a subset of the plurality of heads can provide a plurality of disease predictions respectively for a plurality of different and distinct diseases. For example, a model can include N heads that provide respective disease predictions for N different diseases.

As another example, in some implementations, at least a subset of the plurality of heads can provide a plurality of severity classification predictions respectively for a plurality of different levels of severity of a single disease. For example, a number of different severity levels can be associated with a disease. Each head can provide a respective prediction as to whether the patient is within the corresponding severity level.

In one particular example, the plurality of severity classification predictions respectively for the plurality of different levels of severity of the single disease can be five classification predictions respectively for five levels of an International Clinical Diabetic Retinopathy Disease Severity Scale for diabetic retinopathy.

In another particular example, the plurality of severity classification predictions respectively for the plurality of different levels of severity of the single disease can be a plurality of classification predictions respectively for a plurality of ranges of hemoglobin Alc (e.g., <6%, 6-7%, 7-8%, 8-9%, >9%).

In some implementations, during training, the one or more machine-learned disease detection models can be trained using one or more multi-task or ancillary tasks to improve model performance. As one example, the one or more machine-learned disease detection models can be configured to additionally attempt to predict, during training, demographic data for the patient at issue.

The systems and methods described herein provide a number of technical effects and benefits. More particularly, the systems and methods of the present disclosure provide improved techniques for providing a diagnosis (e.g., differential or non-differential diagnosis) of eye or systemic conditions based on external images of an anterior portion of an eye of a patient using a machine-learned disease detection model. In addition, the information provided by the machine-learned disease detection model can improve the accuracy of diagnoses and patient outcomes. As such, the disclosed system can significantly reduce the cost and time needed to provide diagnostic information and can result in improved medical care for patients.

In particular, the present disclosure provides machine learning systems which perform disease detection and/or diagnosis (e.g., including detecting diabetes-related conditions (e.g., poor sugar control, severity and type of diabetic retinal disease)) from external images of the eye. The example experimental results contained in the incorporated provisional applications show that example implementations of the proposed systems were significantly better at predicting these disease states than using demographic information and medical history (such as years with diabetes) alone, and remained significantly better after adjusting for multiple baseline characteristics and within numerous subgroups. Importantly, these results generalized to diverse patient populations, different imaging protocols, and several devices from independent clinics in multiple U.S. states.

The proposed techniques have implications for the large and rapidly growing population of diabetic patients because they do not, in principle, require specialized equipment. Specifically, detection of diabetes-related retinal disease has to date required fundoscopy or the use of a fundus camera to examine the back of the eye through the pupil. This limits disease screening and detection exams to either eye clinics or store-and-forward tele-retinal screening sites where fundus cameras are present—both of which require in-person visits, expensive equipment, and highly trained camera operators. Similarly, a HbA1c measurement requires a visit for an invasive venous blood draw, which can be unpleasant for patients and have multiple potential side effects including bleeding, bruising, and nerve damage. By contrast, the proposed techniques require only a photograph of the front of the eye, and do not require pupil dilation via eye drops.

The example experimental results contained in the incorporated provisional applications further show that even low-resolution images of 75×75 pixels (which is 1% of the resolution of a basic "720p" laptop webcam and 0.1% of the resolution of a standard 8-megapixel smartphone camera) results in adequate performance, suggesting that the resolution requirements for this technique can be easily met. Therefore, disease detection techniques via external eye images can be widely accessible to patients, whether in clinics, pharmacies, or even at home.

The specific use cases for easy identification and monitoring of high-risk diabetic patients are manifold. First, detecting diabetic patients who have difficulty controlling their blood sugar (e.g., >9% HbA1c) may help to reveal which patients are in need of further counseling, additional diabetic resources, and/or medication changes. Similarly, certain diagnoses (e.g. >7% HbA1c) for patients without diagnosed diabetes can assist in identification of asymptomatic patients at risk for early or mild diabetes (e.g., >7% HbA1c) and can help determine which patients may benefit from a confirmatory blood test and early interventions such as lifestyle counseling or medications.

Second, identification of patients at risk for diabetic retinal disease can determine patients who may benefit from ophthalmology follow-up and targeted treatment to avoid diabetes-associated vision loss. If the top 10% of patients with the highest predicted likelihood of various diabetic retinal diseases were examined via fundus photographs, 10-40% could have vision-threatening diabetic retinal disease and 20-70% could have moderate-or-worse diabetic retinal disease that warrant ophthalmology follow-up. Identifying patients remotely who would benefit from in-person specialized eye care and treatment allows for earlier diagnosis, treatment, and better outcomes in these high-risk individuals. In addition, patients who are found to be at significantly lower risk of diabetic retinal disease can avoid the time and resource cost of a work absence and travel to a specialized eye clinic for an in-person examination.

Scientifically, the ability of the proposed systems to generate highly accurate predictions about diabetic disease states from external eye photography is surprising since such images are primarily used to identify and monitor anterior eye conditions, such as eyelid and conjunctival malignancies, corneal infections, and cataracts. There have been no large studies linking HbA1c or diabetic macular edema to conjunctival vessel changes in diabetes. Furthermore, conjunctival vessel assessment for signs of diabetes is not a common clinical practice due to the relatively subjective, time consuming nature of such an evaluation and the option of a more accurate and easier test for the clinician, specifically HbA1c. To verify that these surprising results were reproducible and not an artifact of a single dataset or site, generalizability was examined and confirmed over a number of different populations.

The data used by the disease detection models (e.g., for training and/or inference) can be de-identified data. For example, personally identifiable information, such as location, name, exact birth date, contact information, biometric information, facial photographs, etc. can be scrubbed from the records prior to being transmitted to and/or utilized by the state space models and/or a computing system including the state space models. For example, the data can be de-identified to protect identity of individuals and to conform to regulations regarding medical data, such as HIPAA, such that no personally identifiable information (e.g., protected health information) is present in the data used by the state space models and/or used to train the state space models.

Further to the descriptions above, a user may be provided with controls allowing the user to make an election as to both if and when systems, programs, or features described herein may enable collection of user information (e.g., photographs). In addition, certain data may be treated in one or more ways before it is stored or used, so that personally identifiable information is removed. For example, a user's identity may be treated so that no personally identifiable information can be determined for the user. Thus, the user may have control over what information is collected about the user, how that information is used, and what information is provided to the user.

In some implementations, an entirety of the disease detection model is stored and implemented at a single device (e.g., the patient's device, the medical professional's device, a server device, etc.). In other implementations, some portions of the disease detection model (e.g., the image embedding portion and/or a context component) can be stored and implemented at a first device (e.g., the patient's device or the medical professional's device) while other portions of the disease detection model (e.g., the differential diagnosis portion) can be stored and implemented at a second device (e.g., a server device). In such fashion, certain data such as patient images and/or patient metadata may never leave the local device (e.g., the patient's device). Instead, in such implementations, only an uninterpretable embedding or representation is transmitted from the local device to the server device. This arrangement can improve patient privacy.

In conclusion, the present disclosure has demonstrated the surprising result that external eye images can be used to detect the presence of eye or non-eyes diseases, including several diabetes-related conditions such as poor blood sugar control and various diabetic retinal diseases. The tool can be used in a home, pharmacy, or primary care setting to improve disease screening and help with management of diabetes.

With reference now to the Figures, example embodiments of the present disclosure will be discussed in further detail.

Example Eye Anatomy and Imagery

FIG. 1 provides a graphical depiction of the anatomy of an eye 12. Two anatomical portions of the eye 12 are specifically highlighted. In particular, box 14 shows the posterior (i.e., rear) of the eye, which primarily includes the retina. Imagery that specifically depicts the posterior of the eye is often referred to as a fundus photograph, and one example is shown at 18. In contrast, box 16 shows the anterior (i.e., front) of the eye, which primarily includes the cornea, pupil, iris, and portions of sclera surrounding the iris. An example photograph showing the external anterior portion of the eye is shown at 20.

Example Telemedicine Configurations

Figure 2A:
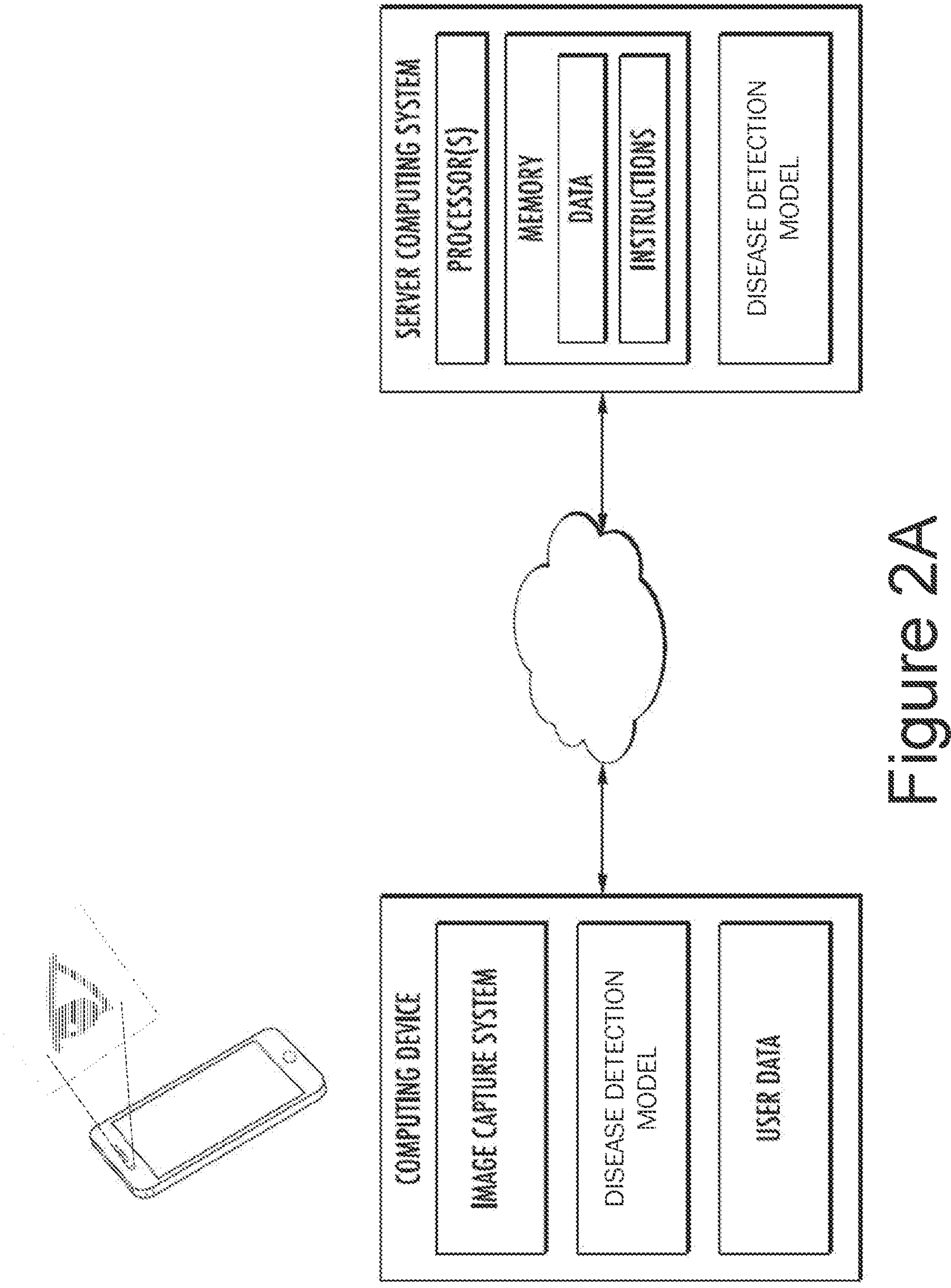
FIG. 2A depicts an example block diagram of a system for providing diagnosis assistance according to example embodiments of the present disclosure.

FIG. 2A depicts an example client-server environment according to example embodiments of the present disclosure. Specifically, FIG. 2A depicts a user computing device and a server system that communicate over a network. The computing device can be a personal electronic device such as a smartphone, tablet, laptop, and so on. The computing device can include an image capture system, at least a portion of a disease detection model, and user data. The image capture system can capture one or more images of a user's anterior eye (e.g., the depicted eye).

In some implementations, the computing device can transmit the captured image(s) to the server computing device. Alternatively or additionally, the disease detection model can include at least a portion of the disease detection model that generates embeddings for one or more images. In this way, the computing device can transmit an embedding representing the image, rather than the image itself. This can reduce the amount of bandwidth needed to transmit the images to the server computing system.

The user data can be stored in a local data storage device and can include user clinical data, user demographic data, and/or user medical history data. This information can be transmitted to the server computing system as needed with user permission. In some examples, the disease detection model at the user computing device can include a context component that generates a feature representation for the user data. In some examples, the disease detection model can combine one or more image embeddings and the feature representation data for the user data.

The server computing system includes some or all of a disease detection model. For example, the server computing system can receive one or more of: image data, one or more embeddings, a unified image representation of multiple embeddings, a feature representation of user data, or a combined representation of unified image representations and a feature representation. Any and/or all of these types of data can be received at the server computing system and used to generate one or more disease detections. The disease detections can be transmitted to the computing device or to another third-party device as needed and approved by the user.

Figure 2B:
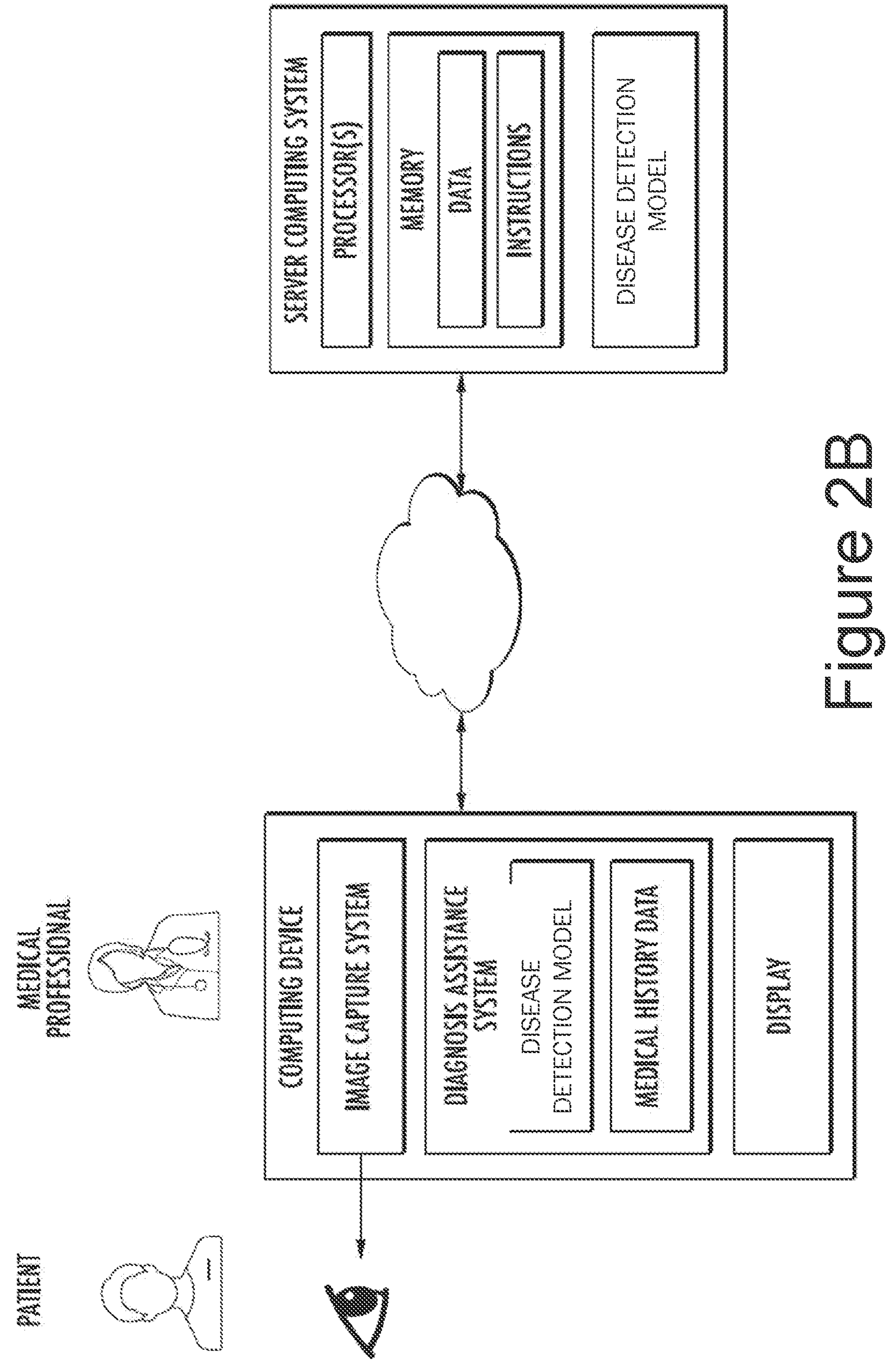
FIG. 2B depicts an example block diagram of a system for providing diagnosis assistance according to example embodiments of the present disclosure.

FIG. 2B depicts an example block diagram of a system for providing diagnosis assistance according to example embodiments of the present disclosure. In this example, the computing device is associated with a medical professional (e.g., a doctor (e.g., optometrist, ophthalmologist, etc.), a nurse practitioner, and so on). The medical professional can utilize the computing device to obtain aid during their diagnostic process. The computing device can include an image capture system (e.g., a camera and associated software), a diagnosis assistance system, and a display. The diagnosis assistance system can include some or all of a disease detection model and medical history data.

The medical professional can use the computing device to capture one or more images of a patient's anterior eye using the image capture system. The diagnosis assistance system can process the imagery locally, generate embeddings locally, or transmit the raw image data to the server computing system. Similarly, medical history data can be processed locally to generate a feature representation or transmitted to the server computing system. In some examples, the diagnosis assistance system includes the full disease detection model and thus can generate disease detections without transmitting data to the server computing system.

In some examples, the diagnostic assistance system transmits data to the server computing system. The disease detection model at the server computing system can generate one or more disease detections and transmit the data back to the diagnosis assistance system for display to the medical professional in the display at the computing device.

Figure 2C:
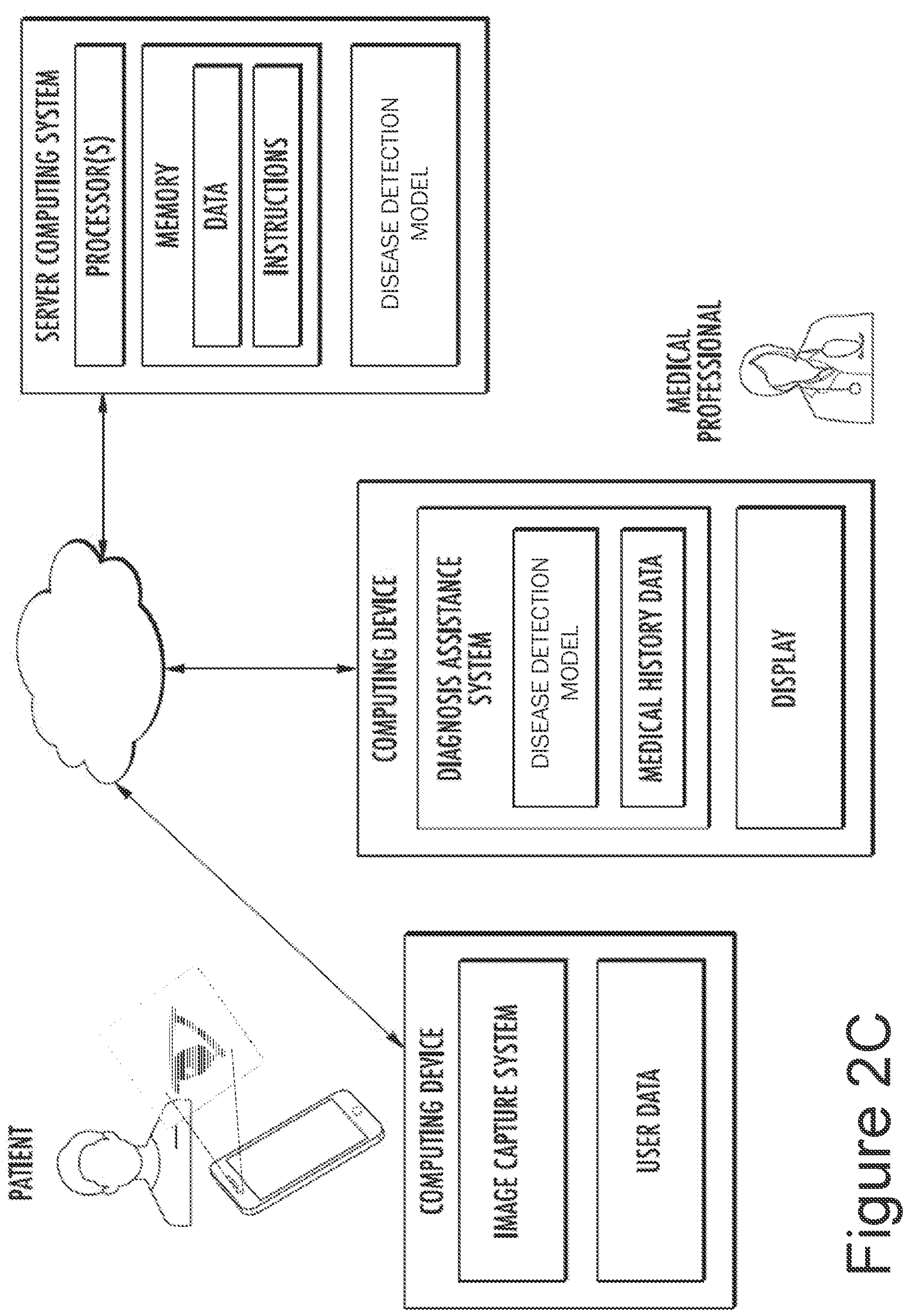
FIG. 2C depicts an example block diagram of a system for providing diagnosis assistance according to example embodiments of the present disclosure.

FIG. 2C depicts an example block diagram of a system for providing diagnosis assistance according to example embodiments of the present disclosure. In this example, the patient is not physically present with the medical professional. Instead, the patient uses a computing device with an image capture system to transmit one or more images (and potentially user data) to the computing device associated with the medical professional and/or the server computing system via a network. Once the computing device receives the one or more images from the computing device associated with the patient, the process can proceed as described above with respect to FIG. 2A or 2B. The medical professional can then transmit any relevant diagnostic information to the computing device of the patient.

Example Model Arrangements

Figures 3, 4:
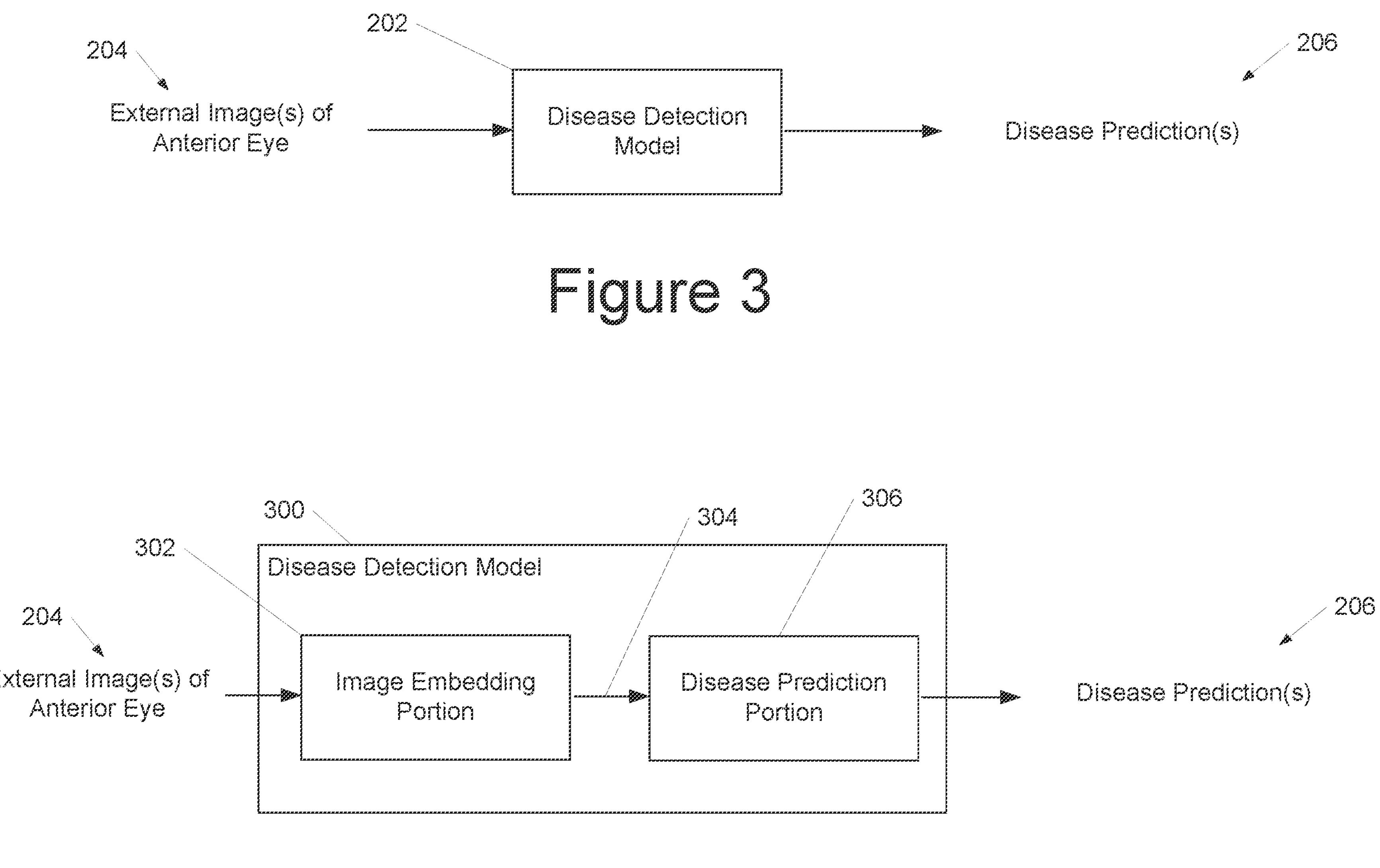
FIG. 3 depicts a block diagram of an example disease detection model according to example embodiments of the present disclosure.
FIG. 4 depicts a block diagram of an example disease detection model according to example embodiments of the present disclosure.

FIG. 3 depicts a block diagram of an example disease detection model 202 according to example embodiments of the present disclosure. In some implementations, the disease detection model 202 is configured to provide disease predictions 206 based on external anterior eye images 204. The one or more machine-learned disease detection models 202 can be trained or configured to provide the disease prediction 206 relative to one or more diseases based on the external eye images 204.

In some implementations of the present disclosure, the one or more machine-learned disease detection models 202 can be trained or configured to provide a disease prediction 206 relative to one or more systemic diseases. Systemic diseases can include diseases which typically affect one or more organ systems and/or present manifestations throughout multiple portions of the body. As examples, the one or more systemic diseases can be or include a blood sugar control disease. For example, the blood sugar control disease can be or include diabetes. As other examples, the one or more systemic diseases can be or include cardiovascular risk or adverse cardiac outcomes, hypertension, anemia, chronic kidney disease, sleep apnea, hypercholesterolemia/atherosclerosis, thyroid disease, hyperparathyroidism, chronic renal failure, gout, lipid control (e.g., elevated lipid levels), and/or other systemic diseases.

In some implementations of the present disclosure, the one or more machine-learned disease detection models 202 can be trained or configured to provide a disease prediction 206 relative to one or more disease manifestations in the eye. For example, the one or more disease manifestations can be or include one or more disease manifestations in a posterior of the eye. As examples, the one or more disease manifestations in the posterior of the eye can be or include diabetic retinopathy, diabetic macular edema, a microaneurysm, glaucoma, age-related macular degeneration, detached retina, cancer of the eye, and/or various forms of retinal disease.

The disease prediction 206 provided by the one or more machine-learned disease detection models 202 can take a number of different formats or measures. As one example, the disease prediction 206 for the patient relative to the one or more diseases can be or include one or more predicted probabilities that the patient is respectively experiencing the one or more diseases. For example, an example disease prediction might indicate that a patient is, with 78% probability, currently experiencing (i.e., diagnosed to have) diabetes.

As another example, the disease prediction 206 for the patient can be or include a predicted evaluation value for the patient. For example, the predicted evaluation value for the patient can be a prediction of a value that would be returned if the patient were evaluated using one or more tests useful for evaluating an eye or non-eye disease. As one example, the disease prediction for the patient relative to the one or more diseases can include a predicted hemoglobin A1c level for the patient, which can, for example, be used to assess or predict a diabetes diagnosis for the patient.

As another example, the disease prediction 206 for the patient relative to the one or more diseases can be or include one or more predicted severity levels respectively for the one or more diseases. For example, an example disease prediction might indicate that a patient is diagnosed with a disease with a particular severity level out of a number of potential severity levels for the disease (e.g., level 2 out of 5 possible levels).

As yet another example, the disease prediction 206 for the patient relative to the one or more diseases can be or include a progression prediction that predicts a time to event for one or more diseases. For example, an example disease prediction might indicate that a patient that is not yet demonstrating disease manifestations may begin demonstrating disease manifestations in six months. Progression predictions (e.g., time to event predictions) can be provided for any number of clinically meaningful events.

The external images 204 can be captured by various different types of devices, including commonly-available cameras (e.g., as opposed to specialized ophthalmoscopes and fundus cameras, thereby enabling more widespread and efficient access to healthcare.

As one example, the one or more external images 204 can be or include one or more images captured by a user device. For example, the user device may be operated by the patient at a time of capture of the one or more images captured by the user device. As examples, the user device can be a camera of a laptop, a camera of a smartphone (e.g., a front facing camera positioned on a same side of the smartphone as a display that depicts a viewfinder for the camera or a rear facing camera on the opposite side), or an external webcam affixed to another user device.

However, although the systems and methods described herein can be used with commonly-available consumer-grade cameras, they can also be used with more sophisticated cameras or imaging devices. As examples, the one or more external images can be or include one or more images captured by a slit lamp camera or a fundoscopic camera operated to capture external anterior eye imagery.

In some implementations, to facilitate successful capture of the external images, a computing system or device (e.g., a user device such as a smartphone) can provide graphical, tactile, and/or auditory user feedback that assists the patient in aligning the anterior portion of the eye with a camera. For example, an image acquisition system can detect an eye/pupil/etc. in real time and can provide the feedback to the user. In one example, the feedback can include periodic audio alerts, where a frequency of the audio alerts increases as the alignment between the eye and camera improves. Directional feedback can be provided as well (e.g., "move the camera upwards").

In some implementations, the image acquisition system can automatically capture an image so that the user does not need to operate the image capture control on the camera device. Alternatively or additionally, the image acquisition system can record a video stream as the user moves the phone in front of their face, and then identify one or more of the video frames which have the best or suitable alignment or appearance (e.g., as measured by some metric including, for example, blurriness, motion, number of pixels attributable to the eye, a machine-learned metric, etc.).

In some implementations, the images 204 provided to the disease detection model(s) 202 can be pre-processed. For example, the one or more external images 204 can be or include cropped portions that have been cropped from one or more larger images. For example, in some implementations, an image that depicts a larger portion of the patient (e.g., the patient's full body or upper torso and head) can be cropped to extract the portion that corresponds to the anterior of the patient's eye. In some implementations, preprocessing the image can include applying a segmentation model to identify and extract only the portions of the image that correspond to the patient's iris and/or pupil. In some implementations, user feedback can be solicited to assist in performing the cropping of the portion of the image that corresponds to the eye.

FIG. 4 depicts a block diagram of an example disease detection model 300 that is a multi-step model for generating disease predictions 206 based on image data 204 according to example embodiments of the present disclosure. The disease detection model 300 is similar to the model 202 depicted in FIG. 3 except that the model 300 includes an image embedding model 302 and a disease prediction model 306. The image embedding model 302 can produce a respective embedding 304 based on each of one or more input images 204. The embedding 304 can be invariant based on angle and lighting. In some examples, the embedding 304 for each input image is a lower dimensional representation of the data in the image (e.g., a numerical vector in an embedding space). The disease prediction model 306 can generate a disease prediction 206 based on the one or more embeddings 304 generated by the image embedding model 302. In some implementations, the embedding model 302 can be placed at one device (e.g., the user's device) while the disease prediction model 306 can be placed at another device (e.g., a medical professional's device). However, the models 302 and 306 can have been trained jointly together (e.g., in a training datacenter and then separately deployed).

Figure 5:
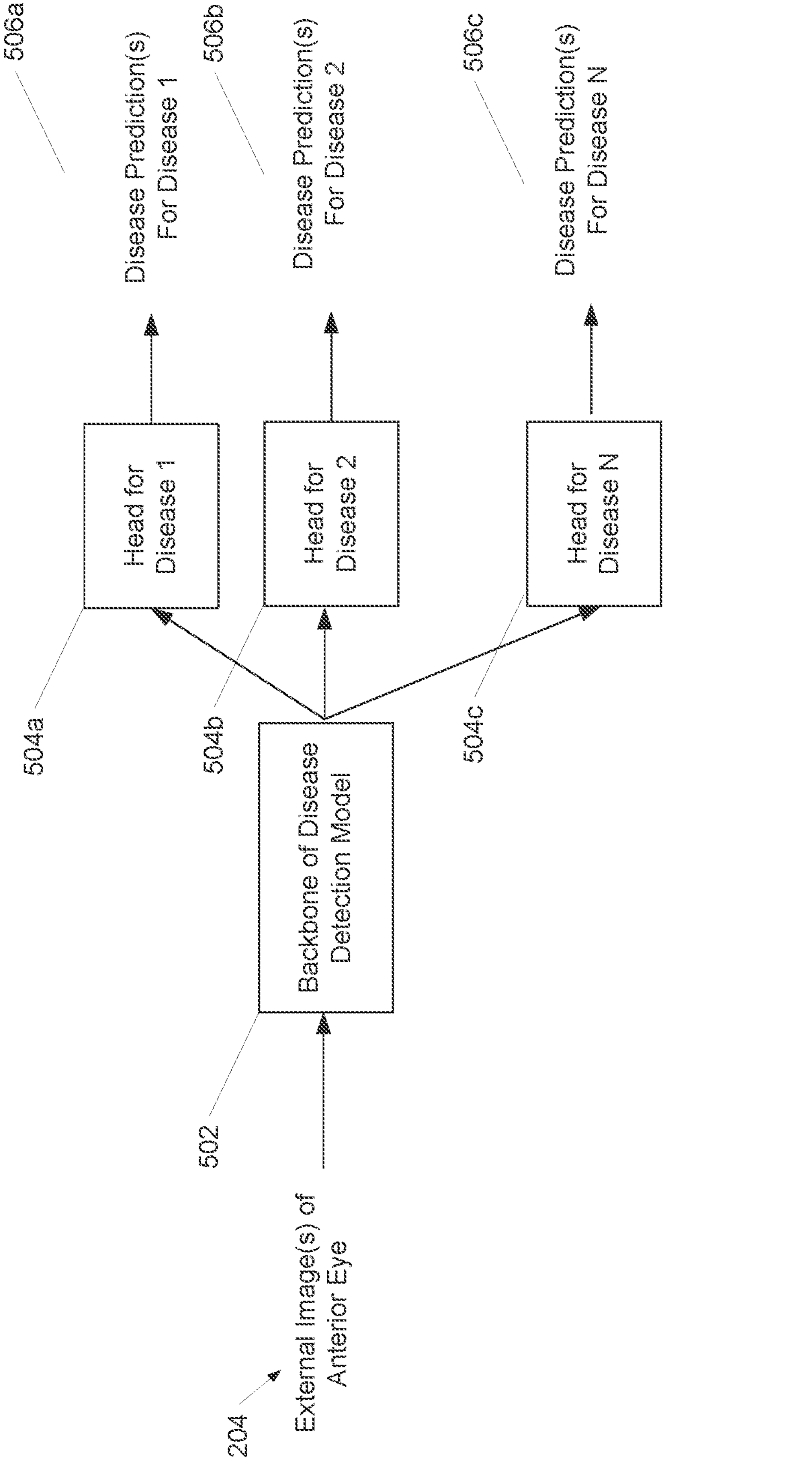
FIG. 5 depicts a block diagram of an example disease detection model according to example embodiments of the present disclosure.

FIG. 5 depicts a block diagram of an example multi-headed disease detection model according to example embodiments of the present disclosure. The disease detection model can include a backbone 502 and a plurality of heads 504*a-c*. The backbone 502 may be the same or similar to the embedding model 302 shown in FIG. 4. The plurality of heads 504*a-c* can provide a plurality of disease predictions 506*a-c* respectively for a plurality of different and distinct diseases. For example, the N heads can provide respective disease predictions for N different diseases.

Figure 6:
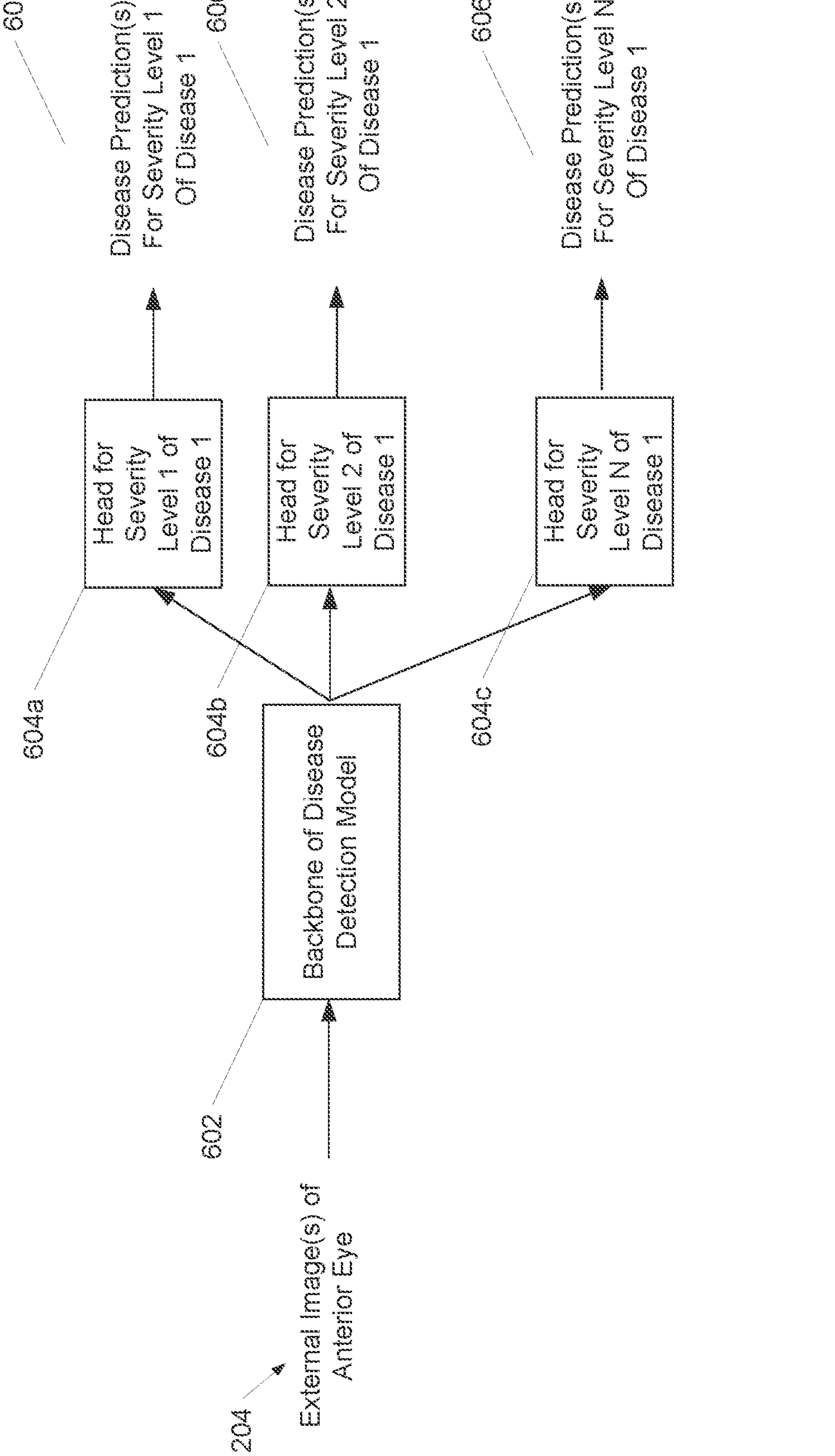
FIG. 6 depicts a block diagram of an example disease detection model according to example embodiments of the present disclosure.

FIG. 6 depicts a block diagram of an example multi-headed disease detection model according to example embodiments of the present disclosure. The disease detection model can include a backbone 602 and a plurality of heads 604*a-c*. The backbone 602 may be the same or similar to the embedding model 302 shown in FIG. 4. The plurality of heads 604*a-c* can provide a plurality of severity classification predictions 606*a-c* respectively for a plurality of different levels of severity of a single disease. For example, a number of different severity levels can be associated with a disease. Each head can provide a respective prediction as to whether the patient is within the corresponding severity level.

The models shown in FIGS. 5 and 6 can optionally be combined. Other heads can be used as well, including during inference and/or during training. As one example, additional head(s) can attempt to predict and the model can be trained on demographic data associated with the patient and/or other information.

Figure 7:
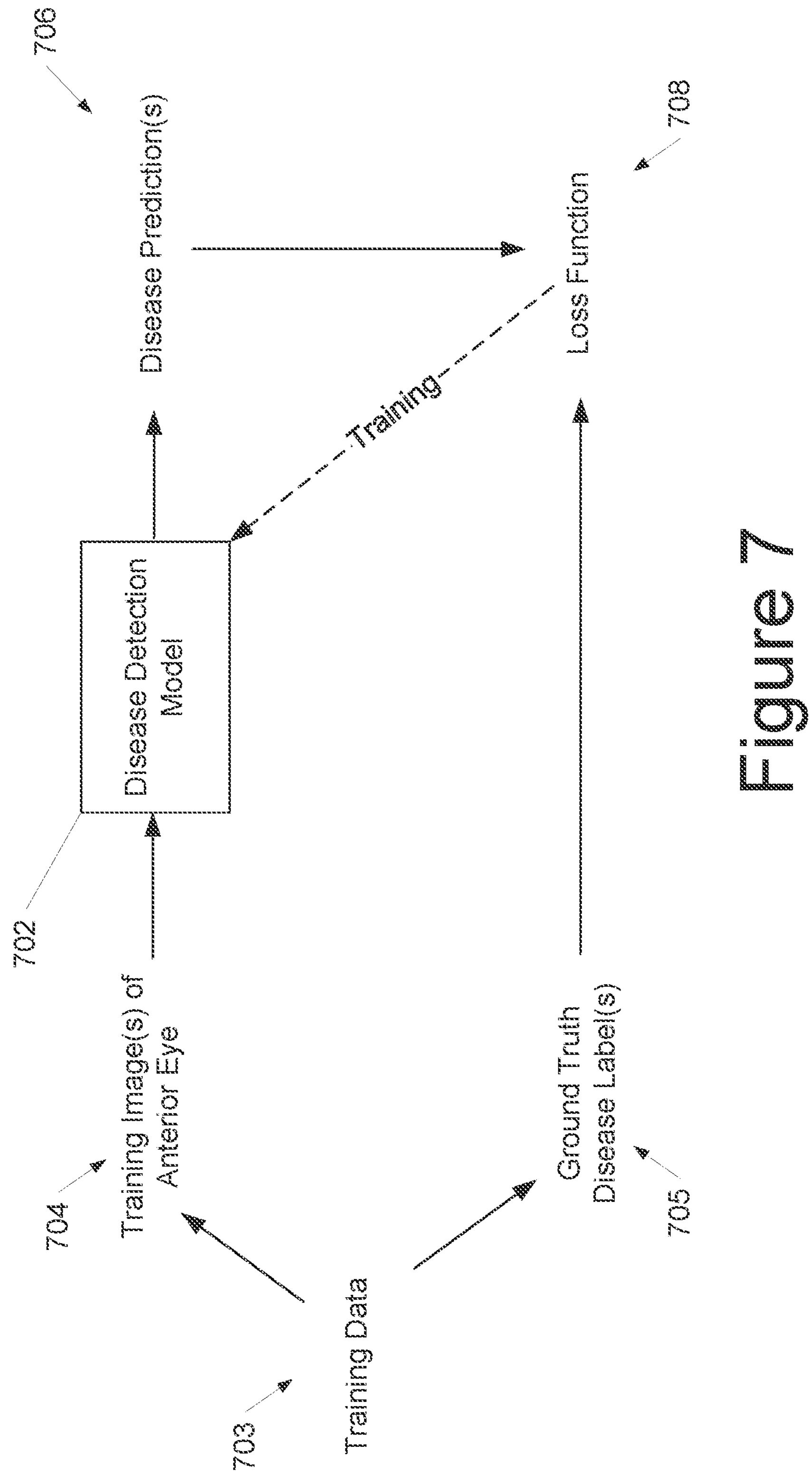
FIG. 7 depicts a block diagram of a process for training an example disease detection model according to example embodiments of the present disclosure.

FIG. 7 depicts a block diagram of a process for training an example disease detection model according to example embodiments of the present disclosure. As depicted in FIG. 7, a computing system can obtain training data 703 that includes one or more external images 704 that depict an anterior portion of an eye of one or more patients and one or more ground truth disease labels 705 that are associated with the one or more external images 704. One or more machine-learned disease detection models 702 can process the one or more external images 704 to generate disease prediction(s) 706 for the patient(s) relative to one or more diseases. The computing system can evaluate a loss function 708 that compares the disease prediction(s) 706 for the patient with the one or more ground truth disease labels 705. The computing system can modify one or more values of one or more parameters of the machine-learned disease detection models 702 based at least in part on the loss function 708 (e.g., by backpropagating the loss function).

Example Devices and Systems

Figure 8A:
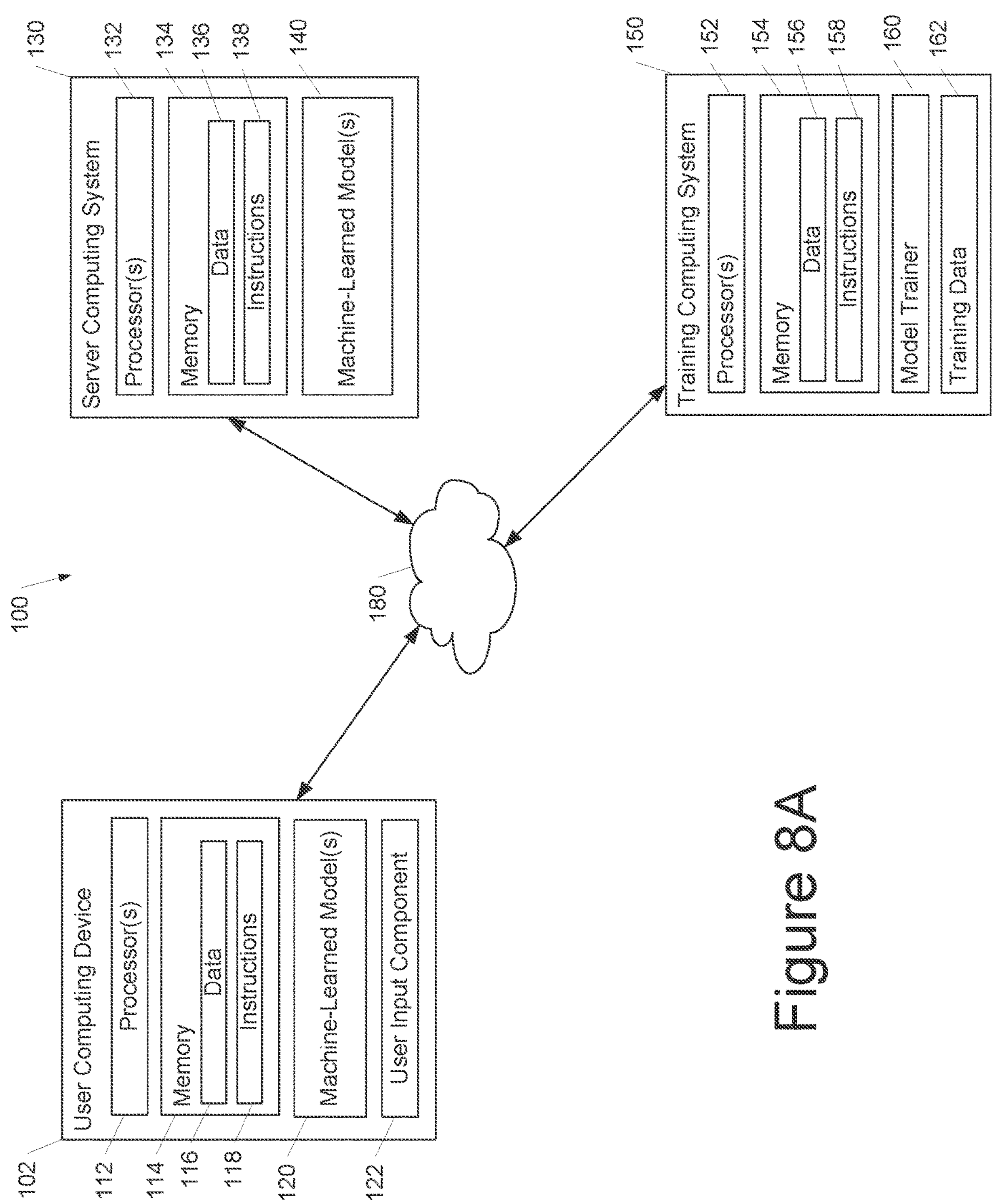
FIG. 8A depicts a block diagram of an example computing system according to example embodiments of the present disclosure.

FIG. 8A depicts a block diagram of an example computing system 100 according to example embodiments of the present disclosure. The system 100 includes a user computing device 102, a server computing system 130, and a training computing system 150 that are communicatively coupled over a network 180.

The user computing device 102 can be any type of computing device, such as, for example, a personal computing device (e.g., laptop or desktop), a mobile computing device (e.g., smartphone or tablet), a gaming console or controller, a wearable computing device, an embedded computing device, or any other type of computing device.

The user computing device 102 includes one or more processors 112 and a memory 114. The one or more processors 112 can be any suitable processing device (e.g., a processor core, a microprocessor, an ASIC, an FPGA, a controller, a microcontroller, etc.) and can be one processor or a plurality of processors that are operatively connected. The memory 114 can include one or more non-transitory computer-readable storage media, such as RAM, ROM, EEPROM, EPROM, flash memory devices, magnetic disks, etc., and combinations thereof. The memory 114 can store data 116 and instructions 118 which are executed by the processor 112 to cause the user computing device 102 to perform operations.

In some implementations, the user computing device 102 can store or include one or more disease detection models 120. For example, the disease detection models 120 can be or can otherwise include various machine-learned models such as neural networks (e.g., deep neural networks) or other types of machine-learned models, including non-linear models and/or linear models. Neural networks can include feed-forward neural networks, recurrent neural networks (e.g., long short-term memory recurrent neural networks), convolutional neural networks or other forms of neural networks. Example disease detection models 120 are discussed with reference to FIGS. 1-7.

In some implementations, the one or more disease detection models 120 can be received from the server computing system 130 over network 180, stored in the user computing device memory 114, and then used or otherwise implemented by the one or more processors 112. In some implementations, the user computing device 102 can implement multiple parallel instances of a single disease detection model 120 (e.g., to perform parallel disease detection across multiple frames of imagery).

Additionally or alternatively, one or more disease detection models 140 can be included in or otherwise stored and implemented by the server computing system 130 that communicates with the user computing device 102 according to a client-server relationship. For example, the disease detection models 140 can be implemented by the server computing system 140 as a portion of a web service (e.g., a disease detection service). Thus, one or more models 120 can be stored and implemented at the user computing device 102 and/or one or more models 140 can be stored and implemented at the server computing system 130.

The user computing device 102 can also include one or more user input components 122 that receives user input. For example, the user input component 122 can be a touch-sensitive component (e.g., a touch-sensitive display screen or a touch pad) that is sensitive to the touch of a user input object (e.g., a finger or a stylus). The touch-sensitive component can serve to implement a virtual keyboard. Other example user input components include a microphone, a traditional keyboard, or other means by which a user can provide user input.

The server computing system 130 includes one or more processors 132 and a memory 134. The one or more processors 132 can be any suitable processing device (e.g., a processor core, a microprocessor, an ASIC, an FPGA, a controller, a microcontroller, etc.) and can be one processor or a plurality of processors that are operatively connected. The memory 134 can include one or more non-transitory computer-readable storage media, such as RAM, ROM, EEPROM, EPROM, flash memory devices, magnetic disks, etc., and combinations thereof. The memory 134 can store data 136 and instructions 138 which are executed by the processor 132 to cause the server computing system 130 to perform operations.

In some implementations, the server computing system 130 includes or is otherwise implemented by one or more server computing devices. In instances in which the server computing system 130 includes plural server computing devices, such server computing devices can operate according to sequential computing architectures, parallel computing architectures, or some combination thereof.

As described above, the server computing system 130 can store or otherwise include one or more disease detection models 140. For example, the models 140 can be or can otherwise include various machine-learned models. Example machine-learned models include neural networks or other multi-layer non-linear models. Example neural networks include feed forward neural networks, deep neural networks, recurrent neural networks, and convolutional neural networks. Example models 140 are discussed with reference to FIGS. 1-7.

The user computing device 102 and/or the server computing system 130 can train the models 120 and/or 140 via interaction with the training computing system 150 that is communicatively coupled over the network 180. The training computing system 150 can be separate from the server computing system 130 or can be a portion of the server computing system 130.

The training computing system 150 includes one or more processors 152 and a memory 154. The one or more processors 152 can be any suitable processing device (e.g., a processor core, a microprocessor, an ASIC, an FPGA, a controller, a microcontroller, etc.) and can be one processor or a plurality of processors that are operatively connected. The memory 154 can include one or more non-transitory computer-readable storage media, such as RAM, ROM, EEPROM, EPROM, flash memory devices, magnetic disks, etc., and combinations thereof. The memory 154 can store data 156 and instructions 158 which are executed by the processor 152 to cause the training computing system 150 to perform operations. In some implementations, the training computing system 150 includes or is otherwise implemented by one or more server computing devices.

The training computing system 150 can include a model trainer 160 that trains the machine-learned models 120 and/or 140 stored at the user computing device 102 and/or the server computing system 130 using various training or learning techniques, such as, for example, backwards propagation of errors. For example, a loss function can be backpropagated through the model(s) to update one or more parameters of the model(s) (e.g., based on a gradient of the loss function). Various loss functions can be used such as mean squared error, likelihood loss, cross entropy loss, hinge loss, and/or various other loss functions. Gradient descent techniques can be used to iteratively update the parameters over a number of training iterations.

In some implementations, performing backwards propagation of errors can include performing truncated backpropagation through time. The model trainer 160 can perform a number of generalization techniques (e.g., weight decays, dropouts, etc.) to improve the generalization capability of the models being trained.

In particular, the model trainer 160 can train the disease detection models 120 and/or 140 based on a set of training data 162. The training data 162 can include, for example, images of anterior portions of eyes that have been labelled with a ground truth disease label.

In some implementations, if the user has provided consent, the training examples can be provided by the user computing device 102. Thus, in such implementations, the model 120 provided to the user computing device 102 can be trained by the training computing system 150 on user-specific data received from the user computing device 102. In some instances, this process can be referred to as personalizing the model.

The model trainer 160 includes computer logic utilized to provide desired functionality. The model trainer 160 can be implemented in hardware, firmware, and/or software controlling a general purpose processor. For example, in some implementations, the model trainer 160 includes program files stored on a storage device, loaded into a memory and executed by one or more processors. In other implementations, the model trainer 160 includes one or more sets of computer-executable instructions that are stored in a tangible computer-readable storage medium such as RAM, hard disk, or optical or magnetic media.

The network 180 can be any type of communications network, such as a local area network (e.g., intranet), wide area network (e.g., Internet), or some combination thereof and can include any number of wired or wireless links. In general, communication over the network 180 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

FIG. 8A illustrates one example computing system that can be used to implement the present disclosure. Other computing systems can be used as well. For example, in some implementations, the user computing device 102 can include the model trainer 160 and the training dataset 162. In such implementations, the models 120 can be both trained and used locally at the user computing device 102. In some of such implementations, the user computing device 102 can implement the model trainer 160 to personalize the models 120 based on user-specific data.

Figure 8B:
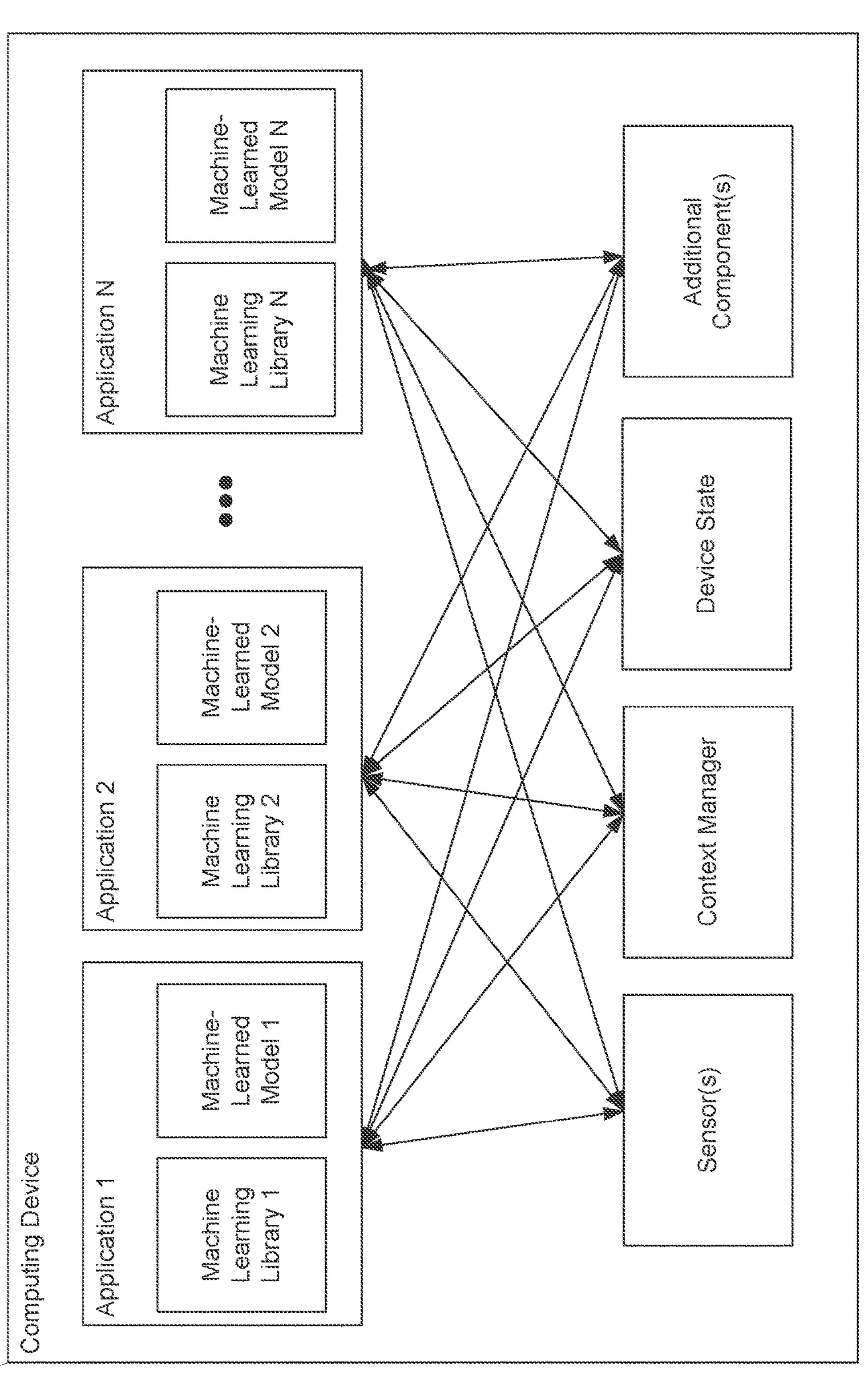
FIG. 8B depicts a block diagram of an example computing device according to example embodiments of the present disclosure.

FIG. 8B depicts a block diagram of an example computing device 10 that performs according to example embodiments of the present disclosure. The computing device 10 can be a user computing device or a server computing device.

The computing device 10 includes a number of applications (e.g., applications 1 through N). Each application contains its own machine learning library and machine-learned model(s). For example, each application can include a machine-learned model. Example applications include a text messaging application, an email application, a dictation application, a virtual keyboard application, a browser application, etc.

As illustrated in FIG. 8B, each application can communicate with a number of other components of the computing device, such as, for example, one or more sensors, a context manager, a device state component, and/or additional components. In some implementations, each application can communicate with each device component using an API (e.g., a public API). In some implementations, the API used by each application is specific to that application.

Figure 8C:
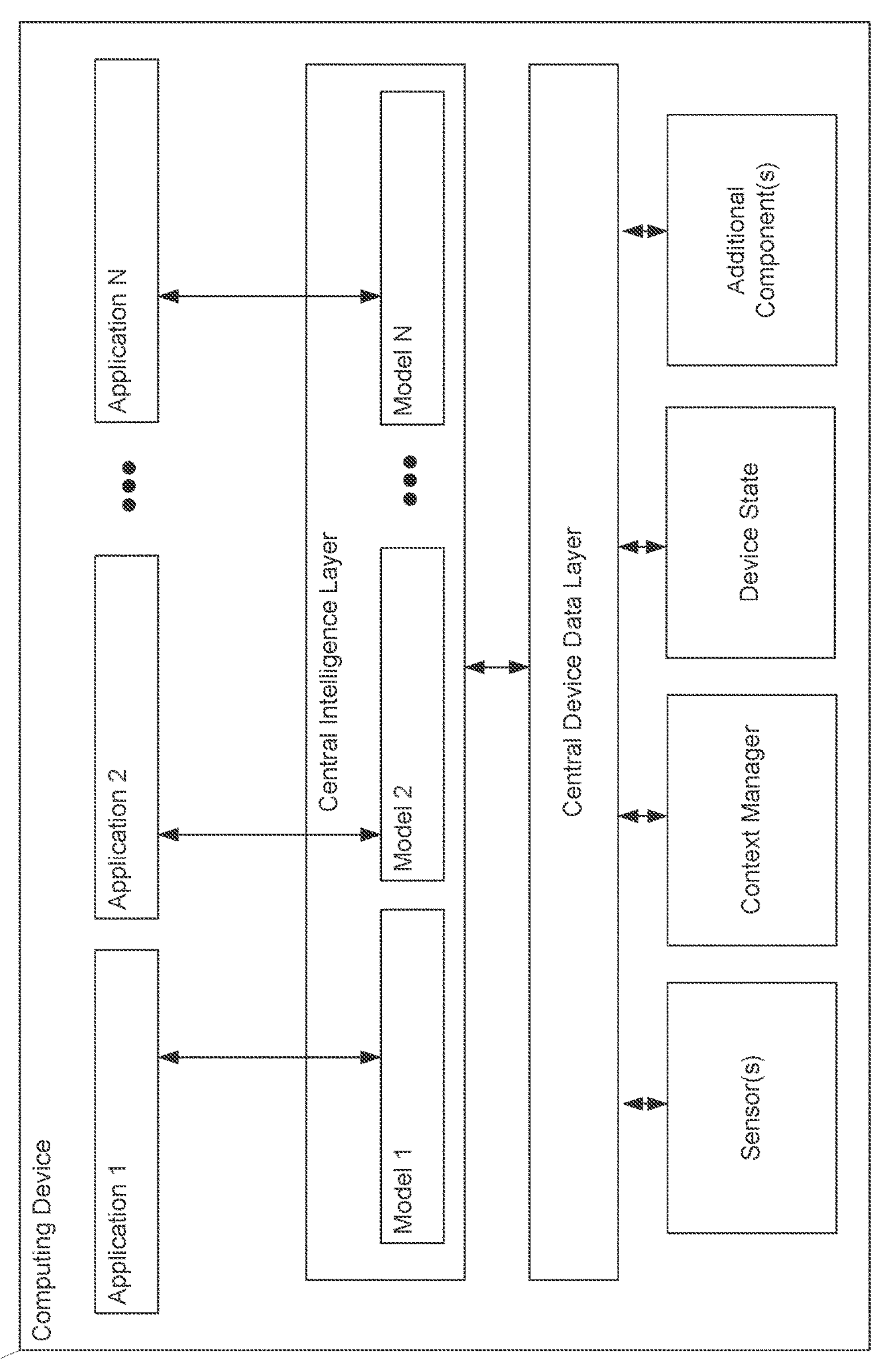
FIG. 8C depicts a block diagram of an example computing device according to example embodiments of the present disclosure.

FIG. 8C depicts a block diagram of an example computing device 50 that performs according to example embodiments of the present disclosure. The computing device 50 can be a user computing device or a server computing device.

The computing device 50 includes a number of applications (e.g., applications 1 through N). Each application is in communication with a central intelligence layer. Example applications include a text messaging application, an email application, a dictation application, a virtual keyboard application, a browser application, etc. In some implementations, each application can communicate with the central intelligence layer (and model(s) stored therein) using an API (e.g., a common API across all applications).

The central intelligence layer includes a number of machine-learned models. For example, as illustrated in FIG. 8C, a respective machine-learned model can be provided for each application and managed by the central intelligence layer. In other implementations, two or more applications can share a single machine-learned model. For example, in some implementations, the central intelligence layer can provide a single model for all of the applications. In some implementations, the central intelligence layer is included within or otherwise implemented by an operating system of the computing device 50.

The central intelligence layer can communicate with a central device data layer. The central device data layer can be a centralized repository of data for the computing device 50. As illustrated in FIG. 8C, the central device data layer can communicate with a number of other components of the computing device, such as, for example, one or more sensors, a context manager, a device state component, and/or additional components. In some implementations, the central device data layer can communicate with each device component using an API (e.g., a private API).

ADDITIONAL DISCLOSURE

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A computing system for detection of diseases from external anterior eye images, the computing system comprising:

one or more processors; and one or more non-transitory computer-readable media that collectively store:

one or more machine-learned disease detection models configured to provide disease predictions based on external anterior eye images; and instructions that, when executed by the one or more processors, cause the computing system to perform operations, the operations comprising:

obtaining one or more external images that depict an anterior portion of an eye of a patient;

processing the one or more external images with the one or more machine-learned disease detection models to generate a disease prediction for the patient relative to one or more diseases, wherein the one or more diseases comprise one or more disease manifestations in the eye, and wherein the one or more disease manifestations in the eye comprise one or more disease manifestations in a fundus of the eye; and providing the disease prediction for the patient relative to the one or more diseases as an output.

2. The computing system of claim 1, wherein the one or more diseases comprise one or more systemic diseases.

3. The computing system of claim 2, wherein the one or more systemic diseases comprise a blood sugar control disease.

4. The computing system of claim 2, wherein the one or more systemic diseases comprise diabetes.

5. The computing system of claim 2, wherein the one or more systemic diseases comprise cardiovascular risk or adverse cardiac outcomes, hypertension, anemia, chronic kidney disease, sleep apnea, hypercholesterolemia/atherosclerosis, thyroid disease, hyperparathyroidism, chronic renal failure, hyperlipidemia, or gout.

6. The computing system of claim 1, wherein the one or more disease manifestations in the fundus of the eye comprise diabetic retinopathy.

7. The computing system of claim 1, wherein the one or more disease manifestations in the fundus of the eye comprise diabetic macular edema.

8. The computing system of claim 1, wherein the one or more disease manifestations in the fundus of the eye comprise one or more microaneurysms in the fundus of the eye.

9. The computing system of claim 1, wherein the one or more disease manifestations in the fundus of the eye comprise glaucoma or age-related macular degeneration.

10. The computing system of claim 1, wherein the disease prediction for the patient relative to the one or more diseases comprises a predicted hemoglobin A1c level for the patient.

11. The computing system of claim 1, wherein the disease prediction for the patient relative to the one or more diseases comprises one or more predicted probabilities that the patient is respectively experiencing the one or more diseases.

12. The computing system of claim 1, wherein the disease prediction for the patient relative to the one or more diseases comprises one or more predicted severity levels respectively for the one or more diseases.

13. The computing system of claim 1, wherein the one or more external images comprise one or more images captured by a user device.

14. The computing system of claim 13, wherein the user device was operated by the patient at a time of capture of the one or more images captured by the user device.

15. The computing system of claim 13, wherein the user device comprises a camera of a laptop or a camera of a smartphone or tablet.

16. The computing system of claim 15, wherein the camera comprises a front facing camera positioned on a same side of the smartphone or tablet as a display that depicts a viewfinder for the camera.

17. The computing system of claim 13, wherein the one or more external images comprise one or more images collected by a slit lamp camera.

18. The computing system of claim 13, wherein the one or more external images comprise one or more images collected by a fundoscopic camera.

19. The computing system of claim 13, wherein the one or more machine-learned disease detection models comprise one or more convolutional or recurrent neural networks.

20. The computing system of claim 13, wherein the one or more machine-learned disease detection models comprise one or more multi-headed neural networks that each have a plurality of heads that respectively output a plurality of predictions.

21. The computing system of claim 20, wherein at least a subset of the plurality of heads that respectively output the plurality of predictions provide a plurality of disease predictions respectively for a plurality of different and distinct diseases.

22. The computing system of claim 21, wherein at least a subset of the plurality of heads that respectively output the plurality of predictions provide a plurality of severity classification predictions respectively for a plurality of different levels of severity of a single disease.

23. The computing system of claim 22, wherein the plurality of severity classification predictions respectively for the plurality of different levels of severity of the single disease comprise five classification predictions respectively for five levels of an International Clinical Diabetic Retinopathy Disease Severity Scale for diabetic retinopathy.

24. The computing system of claim 22, wherein the plurality of severity classification predictions respectively for the plurality of different levels of severity of the single disease comprise a plurality of classification predictions respectively for a plurality of ranges of hemoglobin Alc.

25. The computing system of claim 1, wherein obtaining the one or more external images comprises providing a graphical, auditory, or tactile user feedback that assists the patient in aligning the anterior portion of the eye with a camera.

26. The computing system of claim 1, wherein obtaining the one or more external images comprises detecting and cropping from one or more larger images, image portions that depict anterior portion of the eye of the patient.

27. The computing system of claim 1, wherein the one or more external images comprise one or more images having a resolution of 200×200 pixels or less.

28. A computer-implemented method for training a machine-learned disease detection model to provide disease predictions based on external anterior eye images, the method comprising:

obtaining one or more external images that depict an anterior portion of an eye of a patient, wherein one or more ground truth disease labels are associated with the one or more external images;

processing the one or more external images with one or more machine-learned disease detection models to generate a disease prediction for the patient relative to one or more diseases, wherein the one or more diseases comprise one or more disease manifestations in the eye, and wherein the one or more disease manifestations in the eye comprise one or more disease manifestations in a fundus of the eye;

evaluating a loss function that compares the disease prediction for the patient with the one or more ground truth disease labels; and modifying one or more values of one or more parameters of the machine-learned disease detection models based at least in part on the loss function.

29. One or more non-transitory computer-readable media that collectively store:

one or more machine-learned disease detection models configured to provide disease predictions based on external anterior eye images; and instructions that, when executed by one or more processors, cause a computing system to perform operations, the operations comprising:

obtaining one or more external images that depict an anterior portion of an eye of a patient;

processing the one or more external images with the one or more machine-learned disease detection models to generate a disease prediction for the patient relative to one or more diseases, wherein the one or more diseases comprise one or more disease manifestations in the eye, and wherein the one or more disease manifestations in the eye comprise one or more disease manifestations in a fundus of the eye; and providing the disease prediction for the patient relative to the one or more diseases as an output.

* * * * *